US 7,544,221 B2

(12) United States Patent
Allison et al.

(10) Patent No.: US 7,544,221 B2
(45) Date of Patent: Jun. 9, 2009

(54) TRANSPARENT CANDLE AND METHOD OF MAKING

(75) Inventors: Gerald Allison, East Windsor, NJ (US); Erginio Fernandez, West Patterson, NJ (US); Jonathan Dean, Sussex, NJ (US)

(73) Assignees: Firmenich SA, Geneva (CH); Clearwax LLC, Franklin, NJ (US)

( * ) Notice: Subject to any disclaimer, the term of this patent is extended or adjusted under 35 U.S.C. 154(b) by 336 days.

(21) Appl. No.: 11/489,146

(22) Filed: Jul. 18, 2006

(65) Prior Publication Data

US 2006/0292507 A1   Dec. 28, 2006

Related U.S. Application Data

(63) Continuation of application No. PCT/US2005/001960, filed on Jan. 21, 2005.

(60) Provisional application No. 60/538,363, filed on Jan. 21, 2004.

(51) Int. Cl.
*C10L 7/00* (2006.01)
*C10L 1/19* (2006.01)
*C10L 1/18* (2006.01)
*C10M 105/38* (2006.01)

(52) U.S. Cl. .......................... 44/275; 44/389; 508/485
(58) Field of Classification Search ................ 44/275, 44/389; 508/485
See application file for complete search history.

(56) References Cited

U.S. PATENT DOCUMENTS

| 3,056,818 A | * | 10/1962 | Werber | 554/172 |
| 3,673,226 A | | 6/1972 | Malec | 260/410.6 |
| 3,681,440 A | * | 8/1972 | Gash | 560/263 |
| 5,843,194 A | | 12/1998 | Spaulding | 44/275 |

FOREIGN PATENT DOCUMENTS

DE          10138242 A1  *  2/2003

* cited by examiner

*Primary Examiner*—Glenn Caldarola
*Assistant Examiner*—James Goloboy
(74) *Attorney, Agent, or Firm*—Winston & Strawn LLP

(57) ABSTRACT

Provided herewith is a transparent candle made substantially of tetraesters of di (trimethylolpropane).

10 Claims, No Drawings

TRANSPARENT CANDLE AND METHOD OF MAKING

CROSS-REFERENCE TO RELATED APPLICATIONS

This application is a continuation of International application PCT/US2005/001960 filed Jan. 21, 2005, and claims the benefit of the Jan. 21, 2004 filing date of U.S. Provisional Patent Application 60/538,363. The entire content of each prior application is expressly incorporated herein by reference thereto.

FIELD OF THE INVENTION

The present invention relates to a transparent candle, a base material therefor, and a method of making the base.

BACKGROUND OF THE INVENTION

Burning a candle involves a process that imposes rather stringent requirements upon the candle body material in order to be able to maintain a flame, avoid surface pool ignition, and prevent excessive dripping or the candle body melting. When a candle is burned, the heat of the candle's flame melts a small pool of the candle body material (base material) around the base of the exposed portion of the wick. This molten material is then drawn up through and along the wick by capillary action to fuel the flame. In order to meet the stringent requirements that the candle's body material must possess, the candle should liquefy at or below temperatures to which the candle's material can be raised by radiant heat from the candle flame. If too high a temperature is required to melt the body material, the flame will be starved because insufficient fuel will be drawn up through the wick, resulting in the flame being too small to maintain itself.

On the other hand, if the candle's melting temperature is too low, the candle will drip or, in an extreme case, the entire candle body will melt, dropping the wick into a pool of molten body material, with the potential that the surface of the pool could ignite.

Additionally, in order to meet the stringent requirements upon the candle body material, when molten, the material should have a relatively low viscosity to ensure that the molten material will be capable of being drawn up through the wick by capillary action. Additional desired features may place still further demands on these already stringent requirements. For example, it is generally desirable that the candle body material burn with a flame that is both luminous and smokeless, and that the odors produced by its combustion should not be unpleasant. These features require that the composition used to make such candles meet even further physical requirements.

Furthermore, when transparent candles are desired, additional physical requirements must be met by the composition used to make such candles. Compositions that are presently known for making transparent candles typically have one or more undesirable characteristics. In particular, such compositions typically do not have enough rigidity to form a self-supporting candle, and require some type of container or external support. Such container candles generally additionally possess undesirable characteristics such as the potential for the gel compositions from which they are made shifting, for example, during shipping. Known compositions for making transparent candles also typically have an undesirable gelatinous or oily feeling. In addition, such compositions may darken or smoke during burning, which is aesthetically undesirable.

Transparent candles made from candle base materials of the prior art may also exhibit undesired external cracking and/or internal fractures. There is a need for a transparent candle with improved performance characteristics.

SUMMARY OF THE INVENTION

In one aspect, the present invention relates to a transparent palm candle in which the candle base material is an ester of structure I,

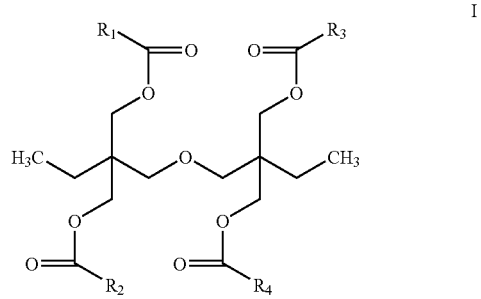

in which the R groups are, independently, $C_9$ to $C_{29}$ alkyl groups, especially $C_{13}$, $C_{15}$, and $C_{17}$ alkyl groups. The base ester material can be combined with a variety a functional and aesthetic additives as is known in the art.

In another aspect, the present invention relates to a method of making the ester candle base material of structure I including the steps of: combining a molar quantity of di (trimethylolpropane), an esterification catalyst, and a molar quantity equal to at least about four times the molar quantity of di (trimethylolpropane) of at least one fatty acid of formula RCOOH, wherein R is a linear or branched alkyl group having about 9 to about 29 carbon atoms; heating the combination to a reaction temperature for a reaction time, during which reaction time a molar quantity of water equal to about four times the molar quantity of combined di (trimethylyolpropane) is distilled-off; and isolating the ester of structure I.

DETAILED DESCRIPTION OF THE INVENTION

As used herein in connection with a measured quantity, about refers to that variation in the measured quantity as would be expected by one skilled in the relevant art performing the measurement and exercising a level of care commensurate with the objective of the measurement and the equipment used.

As used herein in connection with color, APHA refers to the well-known Gardner color scale.

As used herein in connection with the transparent candle of the present invention, transparent connotes a substantial absence of cloudiness or obscurity, so that the body of the candle features an ability to let light pass through in a substantially unobstructed manner, and an ability to have colorant added to the composition without causing cloudiness or reducing the candle's ability to let light pass through in a fairly unobstructed manner. In preferred embodiments, transparent refers to a candle fabricated using the inventive ester of the present invention and having light transmission in a 4 inch thickness of at least about 80%. To add yet one more demand on transparent candle compositions, it would also be desirable if the transparent candles could be used as a fragrance carrier composition for dispersing selected fragrances such as insect repellents.

As used herein in connection with the transparent candle of the present invention, burn rate refers to the combustion consumption rate, measured in grams per hour, and measured by the relevant ASTM method. Transparent candles of the present invention have a burn rate of about 3 to about 5 g/hr.

In one embodiment, the present invention provides a transparent candle fabricated in substantial part from raw materials derived from renewable botanical sources. Such candles are referred to herein as transparent palm candles or simply transparent candles. Although the various parts of many varieties of palm are a rich source of raw materials useful in the practice of the present invention, the designation palm does not require that the raw materials in fact be derived in whole or even in part from the palm.

The transparent palm candle of the present invention is fabricated substantially of an ester of di (trimethylolpropane) of structure I. Made substantially of connotes that the candle includes at least about 50% and preferably at least about 80% of an ester of structure I.

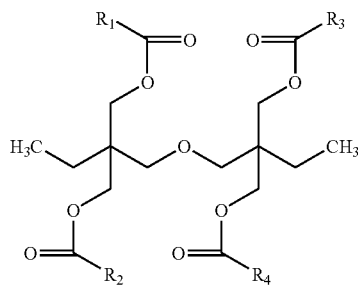

I

In structure I, each of $R_1$, $R_2$, $R_3$, $R_4$ can be a linear or branched alkyl group having about 9 (a $C_9$ alkyl group) to about 29 (a $C_{29}$ alkyl group) carbon atoms. The skilled artisan will understand that in the designation of an alkyl group as group, "n" is a nominal value, substantially and preferably a whole number.

Especially in embodiments in which commercially available raw materials derived substantially from natural botanical sources are used in the practice of the present invention, however, a $C_n$ alkyl group can include alkyl groups having a few more or a few less than "n" carbon atoms.

In preferred embodiments, $R_1$, $R_2$, $R_3$, and $R_4$ are, independently, $C_{13}$, $C_{15}$ or $C_{17}$ groups. In particularly preferred embodiments, the transparent palm candle of the present invention will be substantially comprised of an ester of structure I in which, on average, about 10% by weight of all R groups, combined, are linear $C_{17}$ alkyl groups; about 35% by weight, combined, of all R groups are linear $C_{13}$ alkyl groups; and about 55% by weight of all R groups, combined, are linear $C_{15}$ alkyl groups. Of course, any randomly-selected, individual molecule in a sample of the ester of structure I may contain a higher or lower percentage of a particular linear $C_n$ alkyl group as long as the average value of "n" for a statistically significant number of molecules corresponds substantially to the recited percentages.

The choice of R groups in structure and their relative percentages, depends, inter alia, on whether the candle to be made is a free-standing pillar type or a container type. The ratio of palmitic to stearic is preferably 70% palmitic and 30% stearic.

The transparent palm candles of the present invention are substantially comprised of an ester of structure I (i.e., at least about 50% and preferably at least 80% of the candle is comprised of such ester). The transparent candle of the present invention includes ingredients in addition to the ester of structure I. These ingredients and their function are known to the skilled artisan and described, for example, in U.S. Pat. No. 5,843,194, incorporated herein in its entirety by reference. For example, the transparent palm candle can also include natural paraffin (mainly $C_{14}$ to $C_{30}$ alkanes), synthetic paraffin (e. g. Alpha Olefin Series C-20-30), hydrogenated botanical oils (e. g. soy, coconut, palm, and the like), or a mixture of these.

The transparent candle of the present invention can also include a soot suppressing agent such as known in the art. Hydrogenated SBS (styrene-butadiene-styrene) block copolymers, for example Kraton™ G thermoplastic elastomers (Kraton Polymers, Houston Tex.) can be used for this purpose.

The transparent candle of the present invention can further include a fragrance and, especially, a coloring or appearance-enhancing agent. The transparent candles of the present invention are well suited for the inclusion of colorants and other appearance-enhancing agents.

Fragrances suitable for use in the candles of the present invention include, for example, citronella, AN114351 Sweet Peach, AN114349 Mountain Berry, AN114350 Country Garden, AN114462 Lavender Meadows, AN114463 Strawberries' N Cream and AN114215 Vanilla from Noville Corp., South Hackensack, N.J. Such fragrances are typically added in the range from about 1 wt. to about 5 wt. %, with the level being selected so as to achieve the desired throwing power. An insect repellant can be used instead of or in addition to a fragrance. Non-limiting examples of suitable insect repellants include citronella, dimethyl phthalate and n, n-dimethyl-m-tolumide. The transparent palm candle of the present invention can receive up to 10% to 20% fragrance.

Coloring agents (colorants) and other appearance-enhancing agents, including decorative agents, improve the aesthetics of the candle, including at times when it is burning. Preferably the coloring agent is a liquid dye. However, powder and other forms of dyes may also be used.

Compositions containing one or more coloring agents preferably remain essentially transparent, much like a transparent colored gemstone such as a ruby or emerald.

The transparent compositions of the present invention may also contain one or more decorative materials, which preferably produce a desired aesthetic appearance. Non-limiting examples of types of decorative materials that may be added to the compositions of the present invention include glitter, sparkles, ribbons, small paraffin ornamental characters, and the like.

The transparent palm candle of the present invention can also include a surface tack reducing agent, preferably selected from the group consisting of 12-hydroxystearic acid, 12-hydroxystearic acid methyl ester, 12-hydroxystearic acid ethyl ester, 12-hydroxystearic acid stearyl ester, 12-hydroxystearic acid benzyl ester, 12-hydroxystearic acid amide, isopropyl amide of 12-hydroxystearic acid, butyl amide of 12-hydroxystearic acid, benzyl amide of 12-hydroxystearic acid, phenyl amide of 12-hydroxystearic acid, t-butyl amide of 12-hydroxystearic acid, cyclohexyl amide of 12-hydroxystearic acid, 1-adamantyl amide of 12-hydroxystearic acid, 2-adamantyl amide of 12-hydroxystearic acid, diisopropyl amide of 12-hydroxystearic acid, and mixtures thereof, even more preferably, 12-hydroxystearic acid, isopropyl amide of 12-hydroxystearic acid, and mixtures thereof. Particularly preferred surface-tack-reducing agents include CENWAX™ A which is 12-hydroxystearic acid, or CENWAX™ ME, which is methyl-12-hydroxystearate, and which are available from Union Camp, Jacksonville, Fla. The clear wax formulations may include up to about 4 wt. % of the surface-tack-reducing agent. More preferably, the clear wax formulations include about 0.8 to about 1.5 wt. % of the surface-tack-reducing agent, if present.

Solvents can be used in the formulation and fabrication of the transparent palm candle of the present invention as pillar (free-standing) or container-type candles. Solvents, useful in the manufacture of the candles of the present invention include dibenzoate plus dioctyl, terephthalate, DEHT, bis (2-ethylhexyl) terephthalate, 1,4-benzene dicarboxylic acid, and 2-ethylhexyl ester. Preferred solvents include benzyl benzoate, butyl stearate, octylhydroxystearate, isostearyl alcohol and all natural oils, for example soy and corn oils, to mention just two. Some low molar ethoxylated surfactants can also be employed as solvents for the formulation and manufacture of the clear palm candle of the present invention.

The skilled artisan will know to select, by routine experimentation, the kind and amount of solvent depending on the particular choice or R groups in the ester of structure I, the other additives and ingredients to be used, and the type of candle to be made.

The transparent candle of the present invention does not require at least one wick to burn. However, use of at least one wick is preferred. The at least one wick of the candles of the present invention is made from wicking material. The choice of wicking material is important in making an aesthetically acceptable transparent candle After all, the wick is fully visible. Preferred wicks contain a cotton core which have been observed to provide the most desired combination of burn characteristics, especially with respect to attributes such as smoke, bloom, fragrance throw and burn rate. However, other types of suitable wicks known to those in the art, may also be used in accordance with the present invention. Non-limiting examples of suitable wicks and wicking materials known to those skilled in the art are commercially available from Atkins-Pearce of Covington, Ky. Preferred wicks are HTP/performa series from Atkins & Pierce and those of the FNST2 series from Wedo Germany. Impregnation process with various chemical salts help in the self-trimming of the wick while burning.

In another embodiment, the present invention provides a method of making the ester of structure I including the steps of: combining a molar quantity of di (trimethylolpropane), an esterification catalyst, and a molar quantity equal to at least about four times the molar quantity of di (trimethylolpropane) of at least one fatty acid of formula RCOOH, wherein R is a linear or branched alkyl group having about 9 to about 29 carbon atoms; heating the combination to a reaction temperature for a reaction time, during which reaction time a molar quantity of water equal to about four times the molar quantity of di (trimethylolpropane) combined is distilled-off and; isolating the ester of structure I.

Suitable esterification catalysts include dibutyltin oxide, tetraisopropyl titanate, tosic acid, acid, zinc chloride, boron trifluoride, tannic acid, and sodium hydrogen sulfate. Tetraisopropyl titanate is preferred esterification catalyst.

The combination of di (trimethylolpropane), with and without esterification catalyst, and at least one fatty acid is heated at a reaction temperature, typically 150° C. to 210° C., for a reaction time sufficient to distill-off an amount of water equal to about four times the molar amount of di (trimethylolpropane) combined whereby substantially all of the carboxylic acid groups of all fatty acids present in the combination are esterified. The ester of structure I is isolated by any means known in the art.

EXAMPLE

The present invention and certain of its embodiments are further described in the following non-limiting examples.

Example 1

According to an embodiment of the method of the present invention, a clear palm candle is made according to the following chemical reaction (as represented by the following chemical structures):

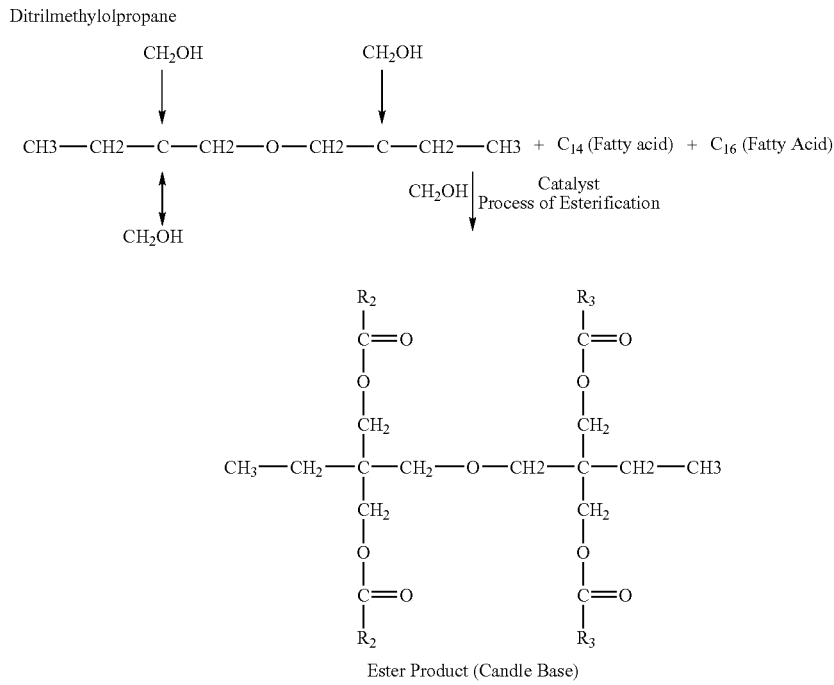

The fatty acids used are: palmitic acid ($C_{16}$ fatty acids); stearic acid ($C_{18}$ fatty acid) myristic acid ($C_{14}$ fatty acid) in the presence of an esterification catalyst (tetra isopropyl titanate) or heat.

Reactants are placed in the reactor (one (1) mole of and four (4) moles of fatty acid; a catalyst is introduced to speed up the rate of reaction). Heat is applied using hot oil as the source of heat. The reactants are cooked for about 16 hours, during which time water of reaction is distilled-off.

Example 2

The following formulations were combined at 140-150° F. and the warm mixture was poured into a wick-containing mold.

Table of Candle Formulations

|   | Base[1] | Benzyl Benzoate | Regalrez 3102 | Regalite 1090 | Reagalite 1010 | Octyl Hydroxy Stearate | Priopol 1009 | Alkyl Benzoate[2] |
|---|---|---|---|---|---|---|---|---|
| 1 | 80% | 10% | — | 10% | — | — | — | — |
| 2 | 80% | 10% | — | — | — | 10% | — | — |
| 3 | 80% | 10% | — | — | — | — | 10% | — |
| 4 | 85% | — | 10% | — | — | — | — | 5% |
| 5 | 80% | — | — | 10% | 10% | — | — | — |

[1] Prepared according to the method of Example 1
[2] $C_{12}$ to $C_{15}$

What is claimed is:

1. A transparent candle comprising an ester of structure I

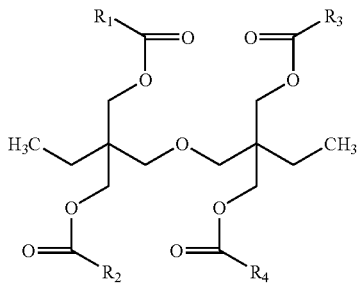

wherein each of $R_1$, $R_2$, $R_3$, and $R_4$, independently, is a linear $C_{13}$, $C_{15}$, $C_{17}$ alkyl group, wherein about 10% by weight of all R groups, combined, are linear $C_{17}$ alkyl groups; about 35% by weight of all R groups, combined, are linear $C_{13}$ alkyl groups; and about 55% by weight of all R groups, combined, are linear $C_{15}$ alkyl groups.

2. The transparent candle of claim 1, having a burn pool temperature of about 55 to 60° C.

3. The transparent candle of claim 1, having an optical transparency of at least 80%.

4. The transparent candle of claim 1, having a color number of about −1 on the Gardner scale.

5. The transparent candle of claim 1, having a burn rate of about 3 to about 5 grams per hour.

6. The transparent candle of claim 1, further comprising at least one synthetic wax, paraffin wax, or hydrogenated oil.

7. The transparent candle of claim 1, further comprising at least one additive selected from the group consisting of: fragrances, coloring agents, insect repellants, and tack-reducing agent.

8. A transparent candle comprising: a) an ester of structure I

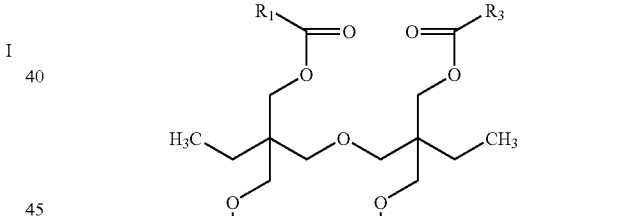

wherein each of $R_1$, $R_2$, $R_3$, and $R_4$, independently, is a linear $C_{13}$, $C_{15}$, or $C_{17}$ group, with the proviso that about 35% by weight of all R groups, combined, are linear $C_{13}$ alkyl groups; about 55% by weight of all R groups, combined, are linear $C_{15}$ alkyl groups, and about 10% by weight of all R groups, combined, are linear $C_{17}$ alkyl groups; b) a surface tack reducing agent, c) a suppressing agent, and d) a synthetic wax or a paraffin wax.

9. The transparent candle of claim 8 further comprising at least one additive that is selected from the group consisting of fragrances and coloring agents.

10. The transparent candle of claim 8 further comprising a wick.

* * * * *

UNITED STATES PATENT AND TRADEMARK OFFICE
CERTIFICATE OF CORRECTION

| | | |
|---|---|---|
| PATENT NO. | : 7,544,221 B2 | Page 1 of 1 |
| APPLICATION NO. | : 11/489146 | |
| DATED | : June 9, 2009 | |
| INVENTOR(S) | : Allison et al. | |

It is certified that error appears in the above-identified patent and that said Letters Patent is hereby corrected as shown below:

Column 8:
Line 55 (line 2 after structure I), after "$C_{13}$, $C_{15}$," insert -- or --.

Signed and Sealed this

Twenty-first Day of July, 2009

JOHN DOLL
*Acting Director of the United States Patent and Trademark Office*